US00PP10992P

United States Patent [19]

Utecht

[11] Patent Number: Plant 10,992

[45] Date of Patent: Jul. 6, 1999

[54] GERANIUM PLANT NAMED 'FIZZARD'

[75] Inventor: Angelika Utecht, Montabaur, Germany

[73] Assignee: Florfis AG, Binningen, Switzerland

[21] Appl. No.: 08/968,044

[22] Filed: Nov. 12, 1997

[51] Int. Cl.[6] ..... A01H 5/00

[52] U.S. Cl. ..... Plt./332

[58] Field of Search ..... Plt./87.12, 332

*Primary Examiner*—Howard J. Locker

*Attorney, Agent, or Firm*—Foley & Lardner

[57] ABSTRACT

A new and distinct cultivar of geranium plant named 'Fizzard', particularly characterized by the combined features of bright red single flowers, very early and rich flowering, medium green foliage with slight zonation, vigorous growth, and bushy and well branched plant habit.

1 Drawing Sheet

The present invention comprises a new and distinct cultivar of geranium, botanically known as *Pelargonium peltatum*, and referred to by the cultivar name 'Fizzard'.

'Fizzard' is a product of a planned breeding program which had the objective of creating new geranium cultivars with bright red flowers, vigorous growth, and well branched plant habit.

'Fizzard' was originated from a hybridization made by the inventor Angelika Utecht in a controlled breeding program in Galdar, Gran Canaria, Spain in 1992. The female parent was hybrid seedling No. 361/23, derived from crossings between an ivy geranium cultivar identified as No. 418 (unpatented), the commercial variety 'Yale' (U.S. Plant Pat. No. 3,874), and St. Malo 19/24 (unpatented). The female parent is characterized by dark red semi-double to double flowers, medium green foliage with weak zonation, and medium to vigorous growth habit.

The male parent of 'Fizzard' was 'Guimo' (unpatented) (commercially known under the name Momo), characterized by single scarlet flowers, large, light to medium green leaves without zonation, good branching ability, and moderately vigorous growth.

'Fizzard' was discovered and selected as one flowering plant within the progeny of the stated cross by Angelika Utecht in 1993 in a controlled environment in Galdar, Gran Canaria, Spain.

The first act of asexual reproduction of 'Fizzard' was accomplished when vegetative cuttings were taken from the initial selection in Autumn 1993 in a controlled environment in Galdar, Gran Canaria, Spain, by, or under the supervision of, Angelika Utecht.

Horticultural examination of plants grown from these cuttings initiated in May, 1994 in Hillscheid, Federal Republic of Germany, and continuing thereafter, has demonstrated that the combination of characteristics as herein disclosed for 'Fizzard' are firmly fixed and are retained through successive generations of asexual reproduction.

'Fizzard' has not been observed under all possible environmental conditions. The phenotype may vary significantly with variations in environment such as temperature, light intensity and daylength, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Fizzard', which in combination distinguish this geranium as a new and distinct cultivar:

1. Bright red flower color.
2. Single flower form.
3. Medium green foliage with weak zonation.
4. Vigorous growth in combination with very good branching characteristics.
5. Very early spring flower response and rich flowering throughout the summer.

Of the many commercial cultivars known to the present inventor, the most similar in comparison to 'Fizzard' is the paternal parent 'Guimo'. Reference is made to attached Chart A which compares certain characteristics of 'Fizzard' to those same characteristics of 'Guimo'.

In general comparison to 'Guimo', 'Fizzard' has a slightly more cherry red, less orange-red hue of flower color, and smaller, somewhat darker green leaves with weak zonation. By contrast, the leaves of 'Guimo' are larger, lighter green without zonation, and differently shaped with serrated margins. Further, 'Fizzard' starts flowering earlier and is more floriferous during the summer.

The accompanying photographic drawing shows typical flower and foliage characteristics of 'Fizzard', with colors being as true as possible with illustrations of this type.

In the following description, color references are made to The Royal Horticultural Society Colour Chart. The color values were determined indoors in from flowers taken from plants grown in a greenhouse in May 1995 in Hillscheid, Germany.

Classification:

*Botanical*.—A hybrid of the species *Pelargonium peltatum*.

*Commercial*.—Ivy geranium, cv. 'Fizzard'.

Inflorescence:

*Umbel*.—Shape: Irregular. Average diameter: 117 mm. Average depth: 45 mm. Peduncle length: 168 mm. Peduncle color: grass-green, about R.H.S. 141 C. Pedicel length: 34 mm. Pedicel color: Dark red to dark violet close to R.H.S. 185 A. Number of flowers per umbel: 10-16.

*Corolla*.—Average diameter: 49 mm. Form: Single. Number of petals: 5. Number of petaloids: 0. Color (general tonality from a distance of three meters): Red. Color of upper surface of petals: 46 B. Markings of upper petals: Black stripes (veins). Color of lower surface of petals: 46 C. Color of sepals: (The sepals are tinged with anthocyanin, the intensity of color is somewhat variable, most intense outdoors) the largest sepal is about R.H.S. 181 A (mainly light red) and the smaller sepals are about R.H.S. 137 D (mainly green). Number of sepals: 5.

*Bud*.—Shape: Narrow elliptic. Color (adaxial): The green part, formed by what are later called sepals, is medium green, R.H.S. 137 D. Color (abaxial): The colored part (later petals) immediately before dividing/unfolding of the petals, is red, R.H.S. 45 A/46 B. Size: Immediately before unfolding, 22 mm in length and 7 mm in width.

*Reproductive organs*.—Androecium: 7 fertile anthers; yellow-orange pollen, white to light pink filaments. Gynoecium: 5-lobed stigma, dark violet with white filament. Seed set: Mainly in late Summer and Autumn.

*Spring flowering response period*.—In Hillscheid, Germany, in 1995 plant had on average 2.3 inflorescences opened 15 weeks after planting of unrooted cuttings (pinched plants).

*Outdoor flower production*.—The flower count in 1994 in Hillscheid, Germany indicated about 41 inflorescences per plant for May through August observation period.

*Durability*.—Average shatter resistance, good rain resistance.

Plant:

*Foliage*. —Form: Ivy-shaped. Margin: Mainly entire, slightly crenated near the tips. Size of leaf: 72 mm. Color of upper surface: Medium green, approximately 137 B. Color of under surface: between R.H.S. 137 D and 143 B. Color of zonation: Narrow ring-shaped zonation, light brown, about 166 A. Tolerance of botrytis: Good.

*General appearance and form*.—Internode length: 40–60 mm. Branching pattern: 9.4 branches after 16 weeks. Average length of plants: 95 cm (in September, based on 35-week old plants, measured from the base of the main stem to the tips of the branches). Habit: mainly drooping.

CHART A

| | FIZZARD | GUIMO |
|---|---|---|
| Flower color, | 46 B | 44 A–45 B |
| Color of leaf | medium green | light to medium |
| Zonation | weak, narrow | absent |
| Beginning of flowering (number of open flowers in 15th week) | 2.3 | 1.0 |
| Flower production | 141 | 116 |

I claim:

1. A new and distinct cultivar of geranium named 'Fizzard', as described and illustrated.

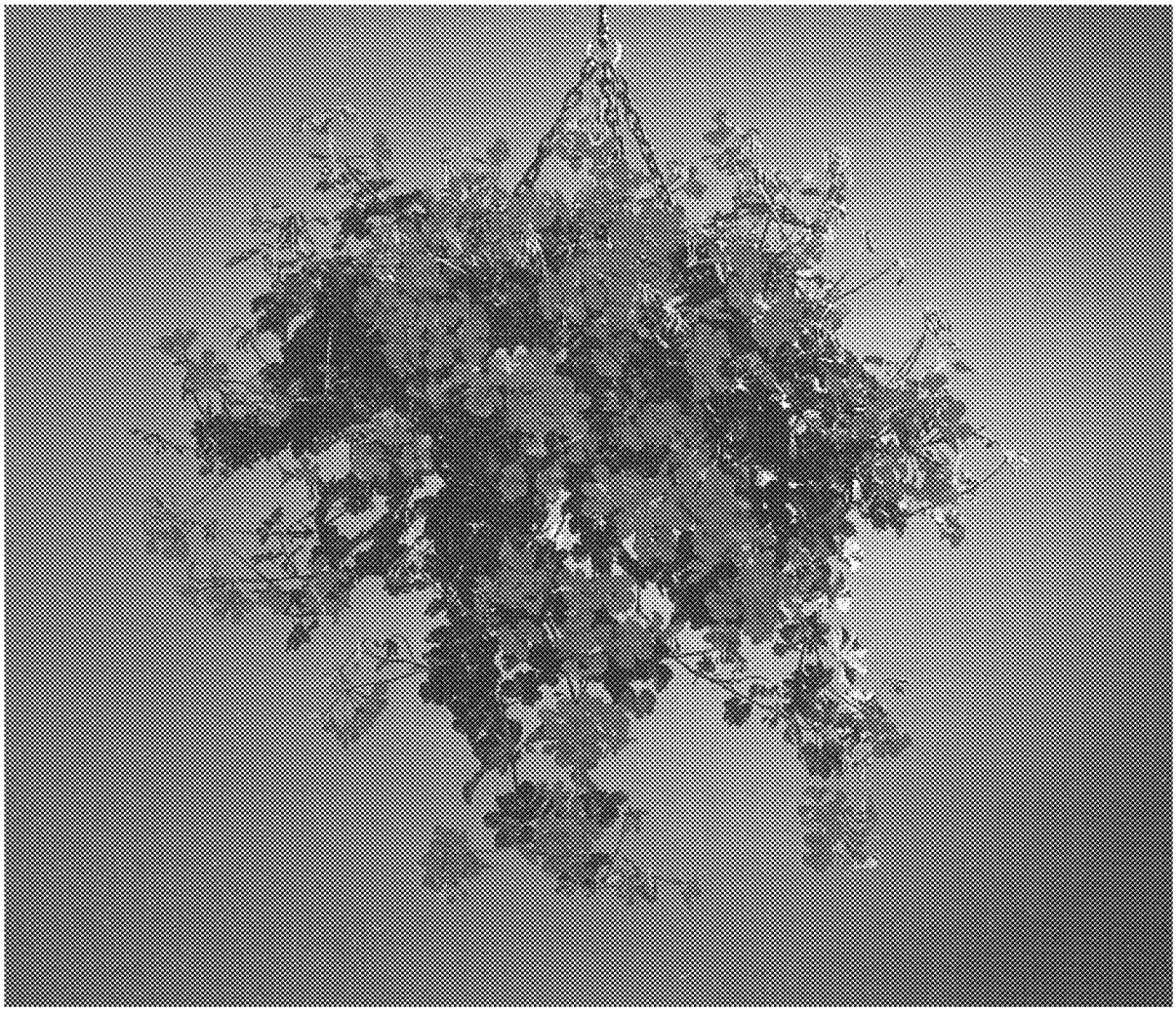

* * * * *